(12) United States Patent
Kumar et al.

(10) Patent No.: US 9,345,773 B2
(45) Date of Patent: May 24, 2016

(54) PVA-BORONIC ACID CONTAINING COPOLYMER COMPOSITIONS FOR PROTEIN DELIVERY

(75) Inventors: Ashok Kumar, Jammu (IN); Rachamalla Maheedhar Reddy, Kadapa-Dt (IN)

(73) Assignee: INDIAN INSTITUTE OF TECHNOLOGY KANPUR, Kanpur (IN)

( * ) Notice: Subject to any disclaimer, the term of this patent is extended or adjusted under 35 U.S.C. 154(b) by 0 days.

(21) Appl. No.: 13/880,299

(22) PCT Filed: Aug. 8, 2011

(86) PCT No.: PCT/IB2011/053523
§ 371 (c)(1),
(2), (4) Date: Apr. 18, 2013

(87) PCT Pub. No.: WO2012/176025
PCT Pub. Date: Dec. 27, 2012

(65) Prior Publication Data
US 2013/0209529 A1 Aug. 15, 2013

(30) Foreign Application Priority Data
Jun. 23, 2011 (IN) .......................... 1773/DEL/2011

(51) Int. Cl.
*A61K 47/32* (2006.01)
*A61K 9/50* (2006.01)
*A61K 9/51* (2006.01)
*A61K 31/78* (2006.01)
*C08F 220/56* (2006.01)
*C08L 33/24* (2006.01)

(52) U.S. Cl.
CPC .............. *A61K 47/32* (2013.01); *A61K 9/5026* (2013.01); *A61K 9/5138* (2013.01); *A61K 31/78* (2013.01); *C08F 220/56* (2013.01); *C08L 33/24* (2013.01)

(58) Field of Classification Search
CPC ..... A61K 9/5026; A61K 47/32; A61K 31/78; C08L 33/24; C08F 220/56
See application file for complete search history.

(56) References Cited

U.S. PATENT DOCUMENTS

| | | | |
|---|---|---|---|
| 4,657,582 | A | 4/1987 | Huber |
| 6,524,274 | B1 | 2/2003 | Rosenthal et al. |
| 6,835,553 | B2 | 12/2004 | Han et al. |
| 2009/0191642 | A1* | 7/2009 | Wang et al. ........................ 436/95 |
| 2010/0029545 | A1 | 2/2010 | Sumerlin et al. |
| 2011/0059176 | A1 | 3/2011 | Moro et al. |

OTHER PUBLICATIONS

Tuncel et al Macromol. Biosci. 2002 p. 214.*
Cimen, Bioeng. Functional Copolymers J. of Applied Polymer Sci. p. 573, 2005.*
Biltai, U., et al., "Strategic approaches for overcoming peptide and protein instability within biodegradable nano- and microparticles," 2008, Eur. J. of Pharm. Biopharm., vol. 59, pp. 375-388.
Brahim, S. et al., "Release Characteristics of Novel pH-Sensitive p(HEMA-DMAEMA) Hydrogels Containing 3010 (Trimethoxysilyl) Propyl Methacrylate," Biomacromolecules, 2003, vol. 4, No. 5, pp. 1224-1231.
Chapekar, M.S., "Tissue engineering: Challenges and opportunities," J. Biomedical Materials Research, 2000, vol. 53, pp. 617-620.
De Geest, B.G. et al., "Glucose-responsive polyelectrolyte capsules," Langmuir., May 2006, vol. 22, No. 11, pp. 5070-5074.
Delie, et al., "Comparison of two methods of encapsulation of an oligonucleotide into poly(,-lactic acid) particles," 2001, Int. J. Pharm. 214, pp. 25-30.
Hisamitsu, I. et al., "Glucose-responsive gel from phenylborate polymer and poly(vinyl alcohol): prompt response at physiological pH through the interaction of borate with amino group in the gel," Pharm. Res., Mar. 1997, vol. 14, No. 3, pp. 289-293.
International Search Report and Written Opinion received for PCT/IB2011/053523 Mailed Dec. 2, 2011.
Ivanov, A.E. et al., "Boronate-containing polymers form affinity complexes with mucin and enable tight and reversible occlusion of mucosal lumen by poly(vinyl alcohol) gel," Int J Pharm, 2008, vol. 358, pp. 36-43.
Ivanov, A.E. et al., "Synthesis of boronate-containing copolymers of N,N-dimethylacrylamide, their interaction with poly(vinyl alcohol) and rheological behaviour of the gels," Polymer, 2004, vol. 45, pp. 2495-2505.
Jaeghere, F. de. et al., "pH-Dependent dissolving nano- and microparticles for improved peroral delivery of a highly lipophilic compound in dogs," 2001, AAPS Pharm. Sci., vol. 3, pp. 92-99.
Kataoka, K., et al., "Sensitive glucose-induced change of the lower critical solution temperature of poly[n,n- dimethylacrylamide-co-3-(acrylamido)phenyl-boronic acid] in physiological saline," 1994, Macromolecules, vol. 27, pp. 1061-1062.
Kikuchi, A. et al., "Glucose-Sensing Electrode Coated with Polymer Complex Gel Containing Phenylboronic Acid," Anal. Chem., 1996, vol. 68, No. 5, pp. 823-828.
Kitano, S. et al., "A novel drug delivery system utilizing a glucose responsive polymer complex between poly (vinyl alcohol) and poly (N-vinyl-2-pyrrolidone) with a phenylboronic acid moiety," J. Controlled Release, 1992, vol. 19, pp. 161-170.
Kitano, S. et al., "Glucose-responsive complex formation between poly(vinyl alcohol) and poly(N-vinyl-2-pyrrolidone) with pendent phenylboronic acid moieties," 1991, vol. 12, No. 4, pp. 227-233.
Kitano, S., et al., "Effect of the incorporation of amino groups in a glucose-responsive polymer complex having phenylboronic acid moieties," 1991, Polym. Adv. Technol. vol. 2, pp. 261-264.

(Continued)

*Primary Examiner* — Suzanne Ziska
*Assistant Examiner* — Thurman Wheeler
(74) *Attorney, Agent, or Firm* — Foley & Lardner LLP

(57) ABSTRACT

Provided herein are phenylboronate containing co-polymers (PCC), compositions containing PCC and polyvinyl alcohol (PVA), such compositions further including proteins, methods of making these compositions by water in oil polymerization, and methods of using the protein containing compositions for releasing proteins. Such phenylboronate containing co-polymers are of Formula I: where m, n, p, x, $R^1$-$R^5$, L, $X^1$ and $X^2$ are defined in the application.

10 Claims, 4 Drawing Sheets

(56) References Cited

OTHER PUBLICATIONS

Kommareddy, S., et al., "Long-circulating polymeric nanovectors for tumor-selective gene delivery," 2005, Technol Cancer Res Treat. vol. 4, pp. 615-625.

Kuzimenkova, M.V., et al., "Boronate-Containing Copolymers: Polyelectrolyte Properties and Sugar-Specific Interaction with Agarose Gel," Macromolecular Bioscience, 2006, vol. 6, pp. 170-178.

Langer, R. et al., "Tissue Engineering," Science, May 14, 1993, vol. 260, pp. 920-926.

Lorand, J. P. et al., "Polyol complexes and structure of the benzeneboronate ion," J. Org. Chem., 1959, vol. 24, pp. 769-774.

Matsumoto, A. et al., "Glucose-Responsive Polymer Bearing a Novel Phenylborate Derivative as a Glucose-Sensing Moiety Operating at Physiological pH Conditions," Biomacromolecules, 2003, vol. 4, No. 5, pp. 1410-1416.

Ozdemir, A. et al., "Boronic acid-functionalized HEMA-based gels for nucleotide adsorption," Journal of Applied Polymer Science, 2000, vol. 78, No. 2, pp. 268-277.

Shiino, D. et al., "Amine containing phenylboronic acid gel for glucose-responsive insulin release under physiological pH," J. Controlled Release, 1995, vol. 37, pp. 269-276.

Shiino, D. et al., "Amine effect on phenylboronic acid complex with glucose under physiological pH in aqueous solution," J. Biomater. Sci. Polym. Ed., 1996, vol. 7, No. 8, pp. 697-705.

Siepmann, J. et al., "A New Mathematical Model Quantifying Drug Release from Bioerodible Microparticles Using Monte Carlo Simulations," Pharmaceutical Research, 2002, vol. 19, pp. 1885-1893.

Wu, C. et al. "Volume phase transition of spherical microgel particles," 1996, Makromol. Chem., vol. 240, p. 123.

Fristrup et al. "Protein repellent hydrophilic grafts prepared by surface-initiated atom transfer radical polymerization from polypropylene," Polym. Chem, 2012, 3, 198-203.

Macková et al. "Colloidally stable surface-modified iron oxide nanoparticles: Preparation, characterization and anti-tumor activity," J. Magn. Magn. Mater. 380 (2015) 125-131.

* cited by examiner

A

B

PVA-BORONIC ACID CONTAINING COPOLYMER COMPOSITIONS FOR PROTEIN DELIVERY

CROSS-REFERENCE TO RELATED APPLICATIONS

This application is a U.S. national stage application under 35 U.S.C. §371 of International Application No. PCT/IB2011/053523, filed on Aug. 8, 2011, which in turn claims the benefit of India Patent Application 1773/DEL/2011, filed on Jun. 23, 2011, the contents of both of which are incorporated herein by reference in their entirety for any and all purposes.

FIELD

This technology is generally related to polymeric materials and more specifically to polymers for cell culturing and scaffolding.

BACKGROUND

For protein delivery, it is desirable to load polymeric nanoparticles and microparticles with proteins. Typically, a protein may be adsorbed on the particle surface or be entrapped within the particle matrix. During the initial phase of protein release or delivery, proteins adsorbed on to the surface may release in an initial burst followed by a slower release phase due to the diffusion of entrapped protein. The protein may also be released from the particles if the constituent polymer is erodible and/or biodegradable. Such polymers, however, face challenges including among others with regard to a high burst release, unpredictable behavior in the later stages of biphasic release profile, overall drug release kinetics, stability during processing, and preservation of the biological activity of the released protein.

SUMMARY

In one aspect, a phenylboronate containing co-polymer (PCC) of Formula I is provided:

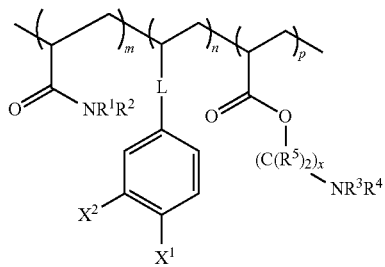

Formula I

In Formula I, m is from 150000 to 220000; n is from 4000 to 6000; p is 0 or from 3500 to 5500; x is from 1 to 5; L is a bond or —CONH— where the carbon is attached to the polymer backbone and the nitrogen is attached to the substituted phenyl ring; $R^1$, $R^2$, $R^3$, and $R^4$ are independently H or $C_1$-$C_6$ alkyl; each $R^5$ independently is H or $C_1$-$C_3$ alkyl; and either $X^1$ is H and $X^2$ is —B(OH)$_2$, or $X^1$ is —B(OH)$_2$ and $X^2$ is H. As used herein, the polymers of the present technology are co-polymers wherein, irrespective of how represented, any constituent monomer may be bonded directly to any constituent monomer, in any order, or next any other monomer, even the same monomer.

In another aspect, a composition is provided that includes polyvinyl alcohol and the PCC of Formula I (a PCC-PVA composition). In another embodiment, the composition further includes a protein and provides a protein containing PCC-PVA composition of the present technology.

In another aspect, a method of preparing a co-polymer is provided. The method includes adding separately to an oil phase, a radical initiator, a compound of Formula II, a compound of Formula III, and a compound of Formula IV to form the mixture:

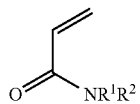

Formula II

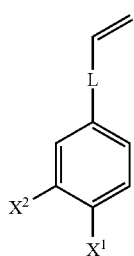

Formula III

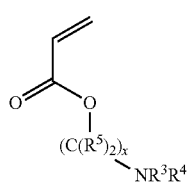

Formula IV where L is a bond or —CONH— wherein the nitrogen is attached to the phenyl ring; $R^1$, $R^2$, $R^3$, and $R^4$ are independently H or $C_1$-$C_6$ alkyl; x is from 1 to 5; each $R^5$ independently is H or $C_1$-$C_3$ alkyl; and either $X^1$ is H and $X^2$ is —B(OH)$_2$, or $X^1$ is —B(OH)$_2$ and $X^2$ is H. The mixture may also include a protein. In one embodiment, the method further includes adding polyvinyl alcohol.

In another aspect, a method is provided for releasing the protein from the polymer compositions which contain the protein. Such methods include contacting the composition with a monosaccharide to release the protein.

BRIEF DESCRIPTION OF THE DRAWINGS

FIGS. 2A and 2B depict poly-(AAm-co-VPBA)-PVA microspheres; FIGS. 2C and 2D depict poly-(NIPAAm-co-VPBA)-PVA nanospheres; FIGS. 2E, 2F, and 2G depict poly-(AAm-co-AAPBA-co-DMAEMA)-PVA microspheres; and FIG. 2H depicts poly-(NIPAAm-co-AAPBA-co-DMAEMA)-PVA nano/microspheres.

FIG. 3A graphically illustrates BSA release from BSA containing poly-(AAm-co-AAPBA-co-DMAEMA)-PVA microspheres; and FIG. 3B graphically illustrates BSA release from poly-(NIPAAm-co-AAPBA-co-DMAEMA)-PVA nano/microspheres.

DETAILED DESCRIPTION

Figure 1:
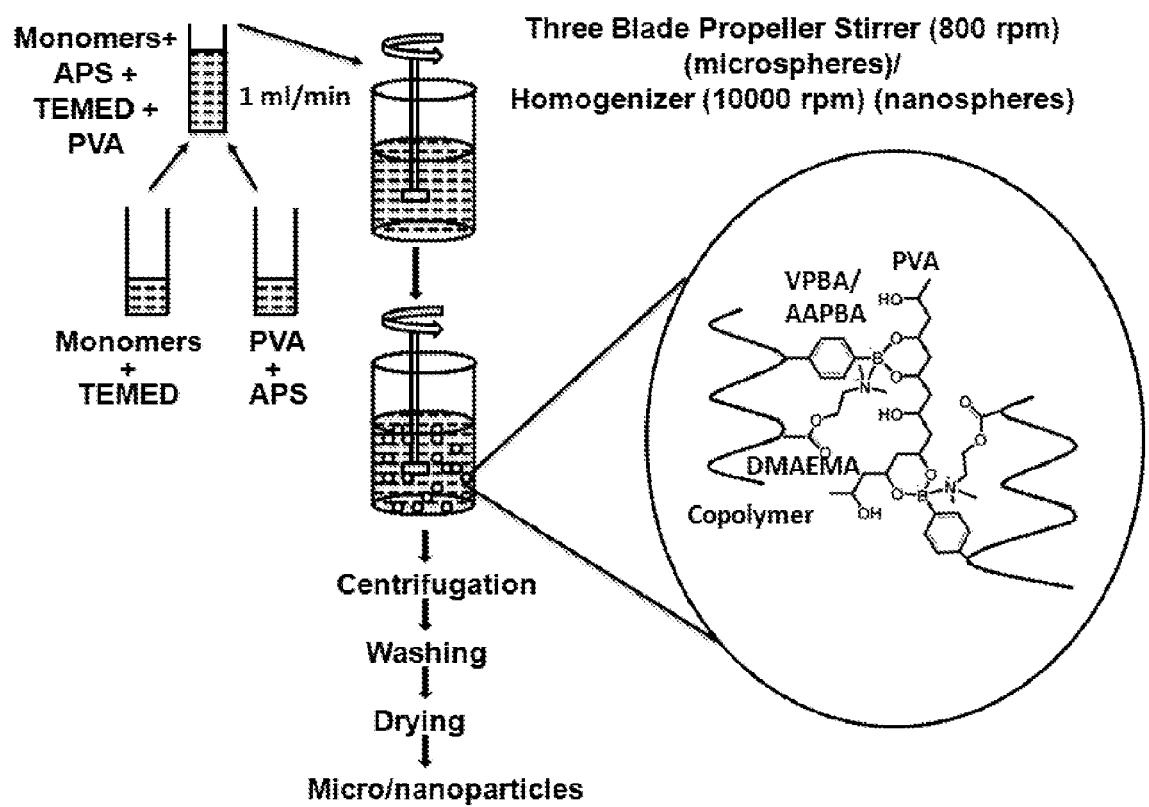
FIG. 1 is a schematic illustration of synthesizing a phenylboronate containing co-polymer-polyvinyl alcohol (PCC-PVA) particulate by water-in-oil (w-o) emulsion polymerization.

In the following detailed description, the illustrative embodiments described are not meant to be limiting. Other embodiments may be utilized, and other changes may be made, without departing from the spirit or scope of the subject matter presented here.

As used herein, unless otherwise stated, the singular forms "a," "an," and "the" include plural reference.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Phenylboronate containing co-polymer (PCC) compositions are provided. The compositions include the PCC and polyvinyl alcohol (PVA). The compositions may also include proteins or other biological materials which may be released from the polymers at a controlled rate. Methods of making these compositions by water in oil polymerization, and methods of using them for releasing proteins are also provided.

In one aspect, the present technology provides a co-polymer of Formula I:

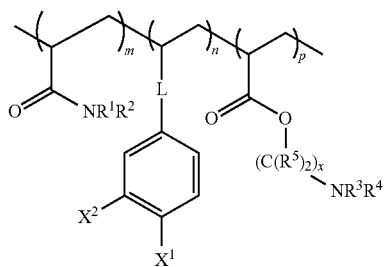

Formula I

In the PCC of Formula I, m is from 150000 to 220000; n is from 4000 to 6000; p is 0 or from 3500 to 5500; x is from 1 to 10; L is a bond or —CONH— wherein the nitrogen is attached to the phenyl ring; $R^1$, $R^2$, $R^3$, and $R^4$ are independently H or $C_1$-$C_6$ alkyl; each $R^5$ independently is H or $C_1$-$C_3$ alkyl; and $X^1$ is H and $X^2$ is —B(OH)$_2$ or $X^1$ is —B(OH)$_2$ and $X^2$ is H.

In another embodiment, $R^1$ and $R^2$ are both H. In another embodiment, $R^3$ and $R^4$ are both H. In another embodiment, $R^1$, $R^2$, $R^3$, $R^4$ are H. In another embodiment, $R^1$ is H, and $R^2$ is $C_1$-$C_6$ alkyl. In another embodiment, $R^3$ is H, and $R^4$ is $C_1$-$C_6$ alkyl. In another embodiment, $R^1$ and $R^2$ are both $C_1$-$C_6$ alkyl. In another embodiment, $R^3$ and $R^4$ are both $C_1$-$C_6$ alkyl. In another embodiment, at least two of $R^1$, $R^2$, $R^3$, and $R^4$ are $C_1$-$C_6$ alkyl and the rest are H. In another embodiment, $R^1$ and $R^2$ are both H, methyl, ethyl, n-propyl, or iso-propyl. In another embodiment, $R^3$ and $R^4$ are both H, methyl, ethyl, n-propyl, or iso-propyl. In another embodiment, $R^1$ and $R^2$ are both H, methyl, ethyl, n-propyl, or iso-propyl, and $R^3$ and $R^4$ are both methyl, ethyl, n-propyl, or iso-propyl. In another embodiment, $R^1$, $R^2$, $R^3$, and $R^4$ are independently H, unsubstituted $C_1$-$C_6$ alkyl, or $C_1$-$C_6$ alkyl substituted with up to 3 substituents selected from the group consisting of hydroxyl, amino, and substituted amino.

In another embodiment, $R^5$ is H. In another embodiment, one of the $R^5$ groups is H and the other $R^5$ group is $C_1$-$C_3$ alkyl.

In another embodiment, L is a bond and $X^1$ is —B(OH)$_2$. In another embodiment, L is —CO—NH— and $X^1$ is H.

In various embodiments, m is from 160,000 to 210,000; from 170,000 to 200,000; or from 180,000 to 190,000. In another embodiment, n is from 4500 to 5500. In another embodiment, n is about 5000. In another embodiment, p is 0. In another embodiment, p is from 4000 to 5000. In some embodiments, x is from 1 to 5.

The co-polymer of Formula I may be, but is not limited to, poly-((AAm)$_m$-co-(VPBA)$_n$); poly-((NIPAAm)$_m$-co-(VPBA)$_n$); poly-((AAm)$_m$-co-(AAPBA)$_n$-co-(DMAEMA)$_p$); poly-((NIPAAm)$_m$-co-(AAPBA)$_n$-co-(DMAEMA)$_p$); poly-((NIPAAm)$_m$-co-(VPBA)$_n$-co-(DMAEMA)$_p$); poly-((AAm)$_m$-co-(VPBA)$_n$-co-(DMAEMA)$_p$); or poly-((DMAAm)$_m$-co-(VPBA)$_n$-co-(DMAEMA)$_p$), wherein m, n, and p are defined as in Formula 1 above. As used herein, -co-, indicates that, as already disclosed hereinabove, these polymers are co-polymers, where any monomer can be directly attached to any monomer, whether it is the same or a different monomer. Such polymers of the present technology may also be represented without explicitly referring to m, n, and p values, for example, and without limitation, as poly-(AAm-co-AAPBA-co-DMAEMA), where it is understood that in the co-polymer the monomers are present in numbers as provided in accordance with the present technology.

In another aspect, a composition is provided that includes polyvinyl alcohol (PVA) and the co-polymer of Formula I (a PCC). The ratio of PVA:PCC may vary from about 1:5 to about 5:1. In some embodiments, the ratio of PVA:PCC is about 1:2 w/w. In some embodiments, the composition may also include molecules or compounds that may be released into cells, tissues, human organs, or non-human organs, in either an in vivo, ex vivo, or in vitro setting. For example, the composition may also include a protein. Examples of various proteins useful in the compositions of the present technology include, without limitation, hormones such as insulin, vasopressin, calcitonin, growth hormone, and luteinizing hormone releasing hormone (LHRH); growth factors such as erythropoietin, insulin-like growth factor, epidermal growth factor, nerve growth factor, and IL-la; cytokines such as interferon α, interferon γ, and interleukin 2; soluble receptors such as tumor necrosis factor receptor (TNF receptor); enzymes such as asparaginase, prolidase, lysozyme, streptokinase, and urokinase; monoclonal antibodies; and peptide vaccines such as group B *Streptococcus* antigen vaccine, tetanus toxoid, diphtheria toxoid, and encephalitis virus vaccine. In other embodiments, the composition also includes other biological material such as DNA, RNA, an aptamer, and the like.

Figure 2:
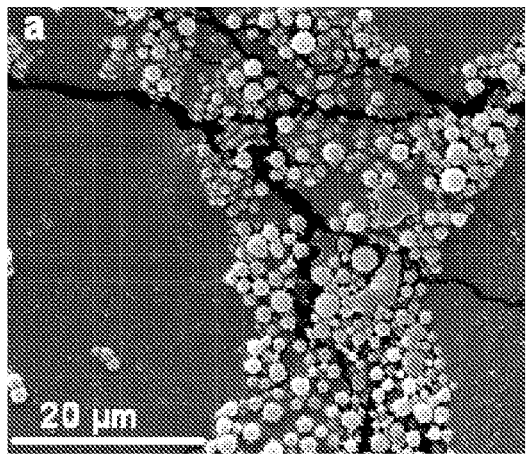
FIGS. 2A-2H are SEM micrographs of PCC-PVA particulates, according to various embodiments.
Figure 2:
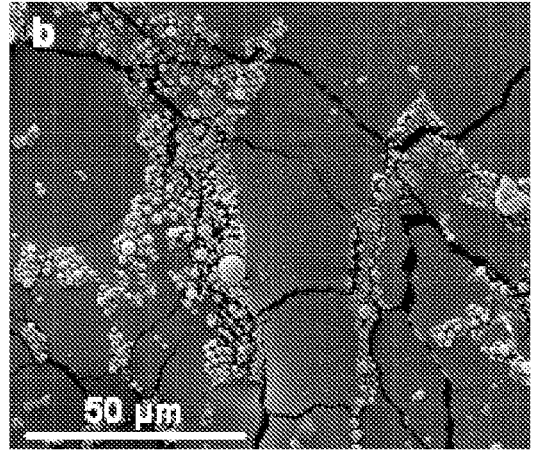
Figure 2:
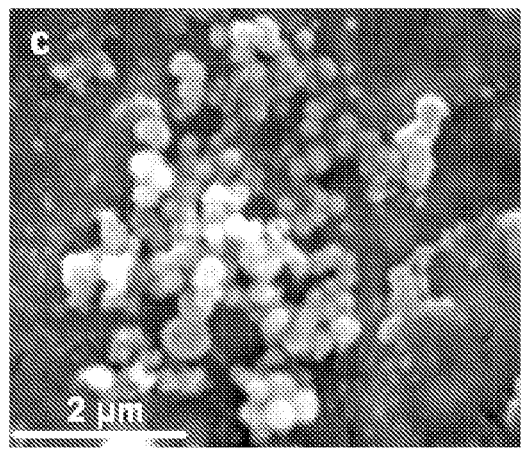
Figure 2:
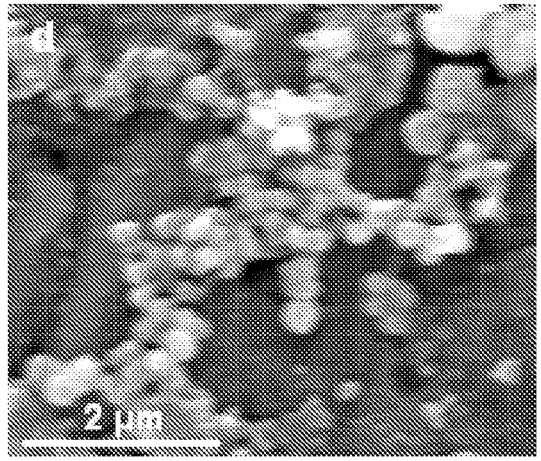
Figure 2:
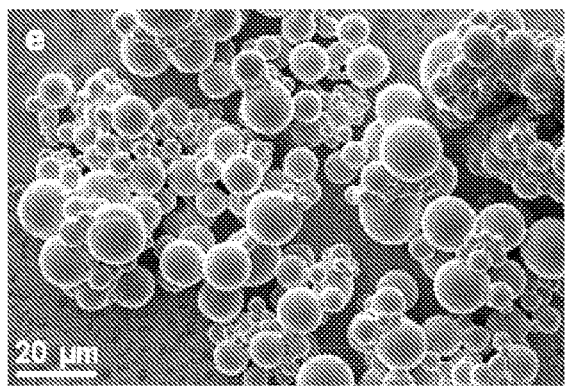
Figure 2:
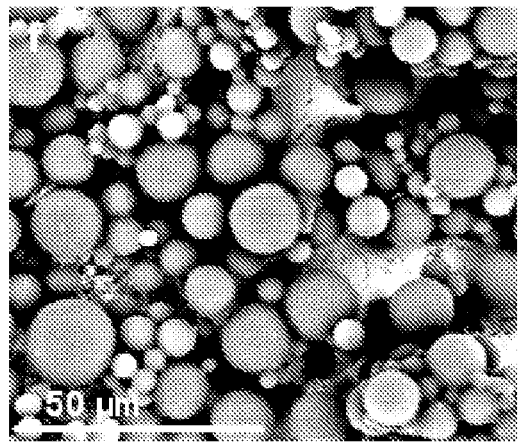
Figure 2:
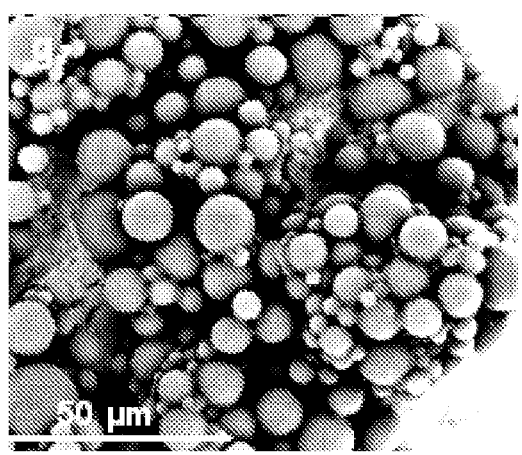
Figure 2:
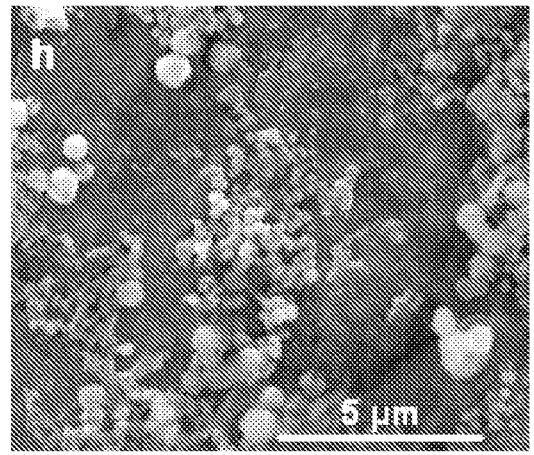

In some embodiments, the PVA-PCC composition is in the form of a micro- or nano-particulate composition. Such particulate compositions may take on a wide variety of shapes, however as shown in FIG. 2, the particulates approximate a spherical shape. In other words, the particles, may not be perfectly spherical, but they generally tend to have a round or oval overall shape. The particles may be solid, or hollow. In some embodiments, the particulate composition is a mixture of microspheres and nanospheres. For example, the individual spheres may be of a size ranging from about 200 nm to about 50 μm, from about 500 nm to about 50 μm, or from about 100 nm to about 5 μm. In other embodiments, the spheres may have an average diameter from about 700 nm to about 1 μm, from about 200 nm to about 1 μm, from about 200 nm to about 300 nm, or from about 1 μm to about 20 μm.

In another aspect, a method of preparing a mixture includes adding separately to an oil phase, a radical initiator, a compound of Formula II, a compound of Formula III, and a compound of Formula IV to form the mixture:

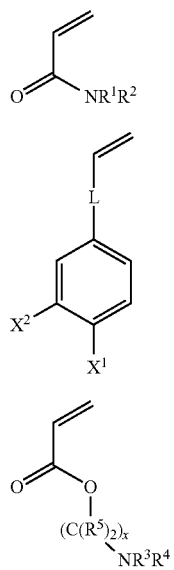

Formula II

Formula III

Formula IV where L is a bond or —CONH— wherein the nitrogen is attached to the phenyl ring; $R^1$, $R^2$, $R^3$, and $R^4$ are independently H or $C_1$-$C_6$ alkyl; x is from 1 to 5; each $R^5$ independently is H or $C_1$-$C_3$ alkyl; and either $X^1$ is H and $X^2$ is —$B(OH)_2$, or $X^1$ is —$B(OH)_2$ and $X^2$ is H.

In another embodiment, the method further includes adding polyvinyl alcohol. In another embodiment, $R^1$, $R^2$, $R^3$, $R^4$, L, $X^1$, $X^2$, and x are defined as in Formula I above. In another embodiment, the ratio of PVA:the monomers is about 1:2 w/w. A variety of radical initiators, polymerization accelerators and polymerization promoters may be used in accordance with the present technology. In one embodiment, the radical initiator includes a persulfate, an azo compound, an azoisoalkylnitrile, and $Fe^{2+}$. In another embodiment, the polymerization accelerator or the polymerization promoter includes N,N,N',N'-tetramethylethylenediamine, an alkylamine or cobalt naphthalene. A variety of oils may be used as the oil-phase, including, without limitation, paraffin oil and vegetable oils, such as, cotton seed oil and sunflower oil. In another embodiment, the mixture further includes a surfactants. A variety of surfactants, including without limitation, Tween and Span, are useful for preparing the compositions of the present technology. In another embodiment, the surfactant is Tween 80 or Span 80.

In another embodiment, the polyvinyl alcohol, the radical initiator, the compound of Formula II, the compound of Formula III, and the compound of Formula IV are added to the oil as aqueous solutions. In another embodiment, the mixture further includes a material such as protein, DNA, RNA, aptamer, or the like, as described above. In another embodiment, the material is trapped within the matrix of the particles as the monomers polymerize. In another embodiment, the protein is surface bound on the particulate. A variety of proteins are useful in the compositions and methods of the present technology. In certain embodiments, the proteins are water soluble proteins. Examples of various proteins useful in the compositions of the present technology include, without limitation, hormones such as insulin, vasopressin, calcitonin, growth hormone, and luteinizing hormone releasing hormone (LHRH); growth factors such as erythropoietin, insulin-like growth factor, epidermal growth factor, nerve growth factor, and IL-1α; cytokines such as interferon α, interferon γ, and interleukin 2; soluble receptors such as tumor necrosis factor receptor (TNF receptor); enzymes such as asparaginase, prolidase, lysozyme, streptokinase, and urokinase; monoclonal antibodies; and peptide vaccines such as group B *Streptococcus* antigen vaccine, tetanus toxoid, diphtheria toxoid, and encephalitis virus vaccine.

Maintaining high DNA concentrations at cell surfaces extends the opportunity for internalization and thereby enhances transfection efficiency. Encapsulation of DNA-vector (viral/non-viral) into a PCC-PVA based micro- and/or nanospheres followed by monosaccharide mediated DNA-vector release from these spheres may serve as an ideal system to achieve high DNA concentrations at the cell surfaces, and with high rates of DNA delivery. The concentrations of DNA at cell surfaces may be controlled by varying the concentration of the monosaccharide solution being administered. As an advantage for cell delivery, monosaccharides such as glucose, fructose, and mannose are free of cell/tissue toxicity.

The process of DNA delivery with analyte responsive PCC-PVA micro- and/or nanospheres may be specifically targeted to particular tissues of interest. By administering monosaccharide solutions into the tissues of interest, targeted DNA release may be achieved. The micro- and/or nanospheres present in non-targeted tissues may remain relatively intact due to the absence of analyte, i.e., monosaccharide, and may get eliminated through a host's excretory systems. Encapsulation of DNA-vector complexes into micro- and/or nanospheres may considerably enhance their half life.

In another embodiment, the method further includes polymerizing the mixture to provide a composition of the present technology, including, without limitation, the microspheres and the nanospheres of the present technology. In another embodiment, the mixture is agitated to polymerize it. In another embodiment, the agitating includes stirring the mixture from 800 rpm to 10,000 rpm. In another embodiment, the agitating includes stirring the mixture from 2,000 rpm to 8,000 rpm, and from 4,000 rpm to 6,000 rpm. Stirring at a lower rpm, e.g., at about 800 rpm, may provide particulates with larger dimensions, such as, microspheres. Stirring at higher rpm, e.g., at about 10,000 rpm, may provide particulates with smaller dimensions, such as, nanospheres. In some embodiments, the mixture may be agitated for about 10 minutes to about 4 hours. Shorter time periods of agitation are sufficient when the agitation involves high-rpm agitation. Longer time periods of agitation are useful when the agitation involves lower-rpm agitation. A variety of apparatus may be used for agitating the mixture. For example, three blade propellers are suitable for agitating at lower rpm. For example, homogenizers are suitable for agitating at higher rpm.

After agitating the mixture for about 10 hours, about 20 hours, or about 30 hours, the mixture may be gently stirred, at rpms much lower than those employed for the agitation to ensure that the polymerization is complete. The polymerization may be carried out at about 2° C., about 5° C., about 8° C., about 10° C., about 15° C., about 20° C., about 25° C., about 30° C., or at about 40° C. Lower temperatures may be used, as long as the mixture does not freeze. The individual components useful for the polymerization may be dissolved in aqueous phases at higher temperatures. The skilled artisan will appreciate upon reading this disclosure that the compositions of the present technology may be separated following routine procedures, such as, centrifugation, washing (e.g., to remove traces of the oil phase and surfactants), and removing residual volatile liquids.

The polymerized mixture can be a particulate, including without limitation, a spherical particulate, such as a microsphere, a nanosphere, or a nano/microsphere, as disclosed hereinabove.

In another aspect, the present technology provides a method of releasing the protein from the compositions of the present technology that contain protein, where the method includes contacting the composition with a monosaccharide to release the protein. The monosaccharide reacts with the polymer to erode the polymer into monomeric or small oligomeric units, which as they release from the particle allow for the concomitant release of the protein, or other entrapped biological material. In another embodiment, the monosaccharide includes glucose, galactose, fructose, sucrose, or arabinose. A variety of proteins may be released in accordance with the present technology, including without limitation, hormones such as insulin, vasopressin, calcitonin, growth hormone, and luteinizing hormone releasing hormone (LHRH); growth factors such as erythropoietin, insulin-like growth factor, epidermal growth factor, nerve growth factor, and IL-1α; cytokines such as interferon α, interferon γ, and interleukin 2; soluble receptors such as tumor necrosis factor receptor (TNF receptor); enzymes such as asparaginase, prolidase, lysozyme, streptokinase, and urokinase; monoclonal antibodies; and peptide vaccines such as group B *Streptococcus* antigen vaccine, tetanus toxoid, diphtheria toxoid, and encephalitis virus vaccine.

If required, the surface bound protein from the particulates may be removed by prior washing of the particulates with deionized water or buffer. Removing such surface bound proteins may eliminate a burst phase protein release, which occur irrespective of the presence of a monosaccharide. In addition to glucose sensitive delivery systems, such particulates may also be used in more general analyte (monosaccharide) responsive controlled protein delivery applications and in growth factor delivery in tissue engineering scaffolds. For example, where growth factors are entrapped within a tissue engineering scaffold, as tissue grows, the growth factor may be released by controlled addition of glucose or other monosaccharide. The tissue engineering scaffolds may incorporate and release growth factors in order to support adequate tissue growth and morphogenesis. The growth factors may get released from the scaffold at specific periods of tissue culture in a sustained manner (rather than abrupt or continuous release throughout the entire tissue growth) to promote growth and morphogenesis. Such controlled release of growth factors at specific points of tissue growth and morphogenesis may be achieved by incorporating growth factor loaded micro- and/or nanospheres into tissue engineering scaffolds. The micro- and/or nanospheres may be incorporated into the scaffold walls either during scaffold fabrication or after the fabrication along with the cells. At specific, desired stages of culture, monosaccharide solutions may be administered into the scaffolds facilitating the controlled release of growth factors from micro- and/or nanospheres, thereby inducing morphogenesis or repair. The timing and the concentration of monomer solution to be employed may depend upon the type of tissues/cells under consideration and the amount of growth factors to be released to induce morphogenesis or repair.

As used herein, "alkyl" groups are monovalent hydrocarbon radicals and include straight chain and branched alkyl groups having from 1 to about 20 carbon atoms, and typically from 1 to 12 carbons or, in some embodiments, from 1 to 8 carbon atoms. As also used herein, "alkyl groups" include cycloalkyl groups as defined below. Examples of straight chain alkyl groups include without limitation methyl, ethyl, n-propyl, n-butyl, n-pentyl, n-hexyl, n-heptyl, and n-octyl groups. Examples of branched alkyl groups include, without limitation, isopropyl, sec-butyl, t-butyl, neopentyl, and isopentyl groups. Alkyl groups may be unsubstituted or substituted. Representative substituted alkyl groups may be substituted one or more times with, for example, amino, carboxyl, thio, hydroxy, cyano, alkoxy, phenyl, and/or F, Cl, Br, and I groups.

As used herein, "alkoxy" refers to an —O-alkyl moiety. Examples of alkoxy groups include, without limitation, methoxy, ethoxy, isopropoxy, and benzyloxy.

As used herein, "cycloalkyl" groups are monovalent cyclic hydrocarbons. Examples of cycloalkyl groups include, without limitation, cyclopropyl, cyclobutyl, cyclopentyl, and cyclohexyl. Cycloalkyl groups may be unsubstituted or substituted.

As used herein "protein" includes polypeptides and peptides.

As used herein, "substituted amino" refers to —NHR$^x$ or —N(R$^x$)$_2$ wherein each R$^x$ independently is alkyl, —CO-alkyl, CO$_2$-alkyl, SO$_2$-alkyl, or two R$^x$ groups together with the nitrogen atom to which they are bonded for a cyclic ring.

The present technology, thus generally described, will be understood more readily by reference to the following example, which is provided by way of illustration and is not intended to limit the present technology.

EXAMPLES

Example 1

Method of Synthesizing the Microspheres and Nanospheres

For water-in-oil (w-o) emulsion polymerization, an aqueous phase with particulate forming precursors is added to an oil phase with appropriate amounts of emulsifiers, and agitated. As a result of the agitation, the aqueous phase gets dispersed into fine droplets resulting in a w-o emulsion. In the present system, the aqueous phase includes the various monomers, ammonium persulfate (APS), N,N,N',N'-tetramethylethylenediamine (TEMED), and PVA. APS and TEMED, are useful as free radical polymerization initiator and promoter. The oil phase is light liquid paraffin oil. APS and TEMED initiate free radical polymerization of monomers. On attaining a sufficient length (or molecular weight) the co-polymer chains are cross linked by PVA resulting in a particulate. After incubating for about 16 h to complete polymerization and crosslinking, the particulates are separated by centrifugation, washed to remove the traces of oil and surfactants and finally dried (FIG. 1).

Example 1

A. Synthesis of Poly-(AAm-co-AAPBA-co-DMAEMA)-PVA Microspheres

N-Acryloyl-3-aminophenylboronic Acid (AAPBA; 25 mg) was dissolved in double-distilled (DD) degassed water (2.5 mL, pH~7.4) at 60° C. for 15-20 min followed by cooling to room temperature. Acrylamide (AAm, 200 mg), N,N-dimethylaminoethylmethacrylate (DMAEMA, 27 µl), and TEMED (5 µl) were completely dissolved in the AAPBA solution (a total monomer concentration of 10%) and nitrogen bubbled through the solution for 20 min. A PVA solution (2.5 mL, 5%, pH~7.4) with APS (3.75 mg) was added to the 2.5 mL of monomer solution. The final solution (5 mL) included of 5% monomers and 2.5% PVA. The solution (5 mL) was quickly added drop wise to 40 mL of an oil phase (38 mL of liquid paraffin light, 0.5 mL of Tween 80 and 1.5 mL of Span 80) which was stirred at 800 rpm with a three blade propeller stirrer (Mahendra Sc. Inst. Mfg. co., Kanpur, India) with a blade diameter of around 8 cm. The stirring was continued for about 2 h. Then the solution was allowed to stand overnight with gentle magnetic stirring. The microspheres formed were recovered from the oil phase by centrifugation at 671×g (HermLe Z 323 K, Germany), washed twice with n-hexane (40 mL) and twice with deionized water (40 mL) to remove the traces of liquid paraffin and surfactants. The particulates (the microspheres) were dried under vacuum for 24 h and stored at 4° C.

Example 1B

Synthesis of Poly-(NIPAAm-co-AAPBA-co-DMAEMA)-PVA Nano/microspheres

These particulates were synthesized in essentially the same manner as those including poly-(AAm-co-AAPBA-co-DMAEMA)-PVA microspheres except that N-isopropylacrylamide (NIPAAm, 200 mg) was used instead of AAm and a stirring at 10,000 rpm, for 20 minutes, with a homogenizer (IKA T25, Germany) was employed in the place of stirring at 800 rpm with help of a three blade propeller stirrer.

Example 2

Synthesis of Protein Containing Particulates

Protein loaded poly-(AAm-co-AAPBA-co-DMAEMA)-PVA microspheres and poly-(NIPAAm-co-AAPBA-co-DMAEMA)-PVA nano/microspheres were synthesized essentially in the same manner as described above, by additionally dissolving 56 mg of bovine serum albumin (BSA) in the AAPBA solution along with monomers and TEMED.

Example 2A

Synthesis of Poly-(AAm-co-VPBA)-PVA Microspheres

AAm (200 mg), 4-vinylphenylboronic acid (VPBA, 50 mg) and TEMED (19 µL) were dissolved in 100 mM NaOH solution (2.5 mL, pH~13) at a 10% w/v ratio. PVA solution (2.5 mL, 5%, pH~13) with APS (15 mg) was added to above monomer solution (2.5 mL). The final 5 mL solution includes of 5% monomers and 2.5% PVA. This solution (3 mL) was quickly added dropwise to an oil phase (38 mL of liquid paraffin light, 0.5 mL of Tween 80 and 1.5 mL of Span 80) which was stirred at 800 rpm with a three blade propeller stirrer. The stirring was continued for about 2 h. Then the solution was allowed to stand for 16 h under gentle magnetic stirring. The microspheres formed were recovered from the oil phase by centrifugation at 671×g (HermLe Z 323 K, Germany), washed twice with n-hexane and deionized water followed by drying under vacuum.

Example 2B

Synthesis of Poly-(NIPAAm-co-VPBA)-PVA Nanospheres

These particulates were synthesized in essentially the same manner as those including poly-(AAm-co-AAPBA-co-DMAEMA)-PVA Microspheres except that NIPAAm (200 mg) was used instead of AAm and a stirring at 10,000 rpm with a homogenizer (IKA T25, Germany) for 20 minutes was employed in the place of stirring at 800 rpm with help of a three blade propeller stirrer for 2 h.

Example 3

Measuring Particulate Size

All particulates were suspended in aqueous phase, drop coated onto copper stubs followed by sputter gold coating and analyzed by scanning electron microscope (SEM). The size of the particulates depend on the size of aqueous droplets formed during emulsification step which in turn may depend on various parameters like initial precursor concentration and type, stirring conditions, emulsifier concentration and the volumes of aqueous as well as oil phases. As disclosed above, the speed of agitation was selected as a parameter to control the particulate size. A three blade propeller stirrer at 800 rpm was used to synthesize particulates with larger dimensions and a homogenizer at 10,000 rpm was used to synthesize particulates with smaller dimensions (Table 1).

TABLE 1

Effect of mixing on the PCC-PVA particulate size

| No. | Material | Type of Agitation | Approximate Particulate Size | Nature of the particulates |
|---|---|---|---|---|
| 1 | Poly-(AAm-co-VPBA)-PVA | Three Blade Propeller, 800 rpm | ~700 nm-1 µm | Microspheres (FIGS. 2a-2b) |
| 2 | Poly-(NIPAAm-co-VPBA)-PVA | Homogenizer, 10,000 rpm | ~200 nm-300 nm | Nanospheres (FIGS. 2c-2d) |
| 3 | Poly-(AAm-co-AAPBA-co-DMAEMA)-PVA | Three Blade Propeller, 800 rpm | ~1 µm-20 µm | Microspheres (FIGS. 2e-2g) |
| 4 | Poly-(NIPAAm-co-AAPBA-co-DMAEMA)-PVA | Homogenizer, 10,000 rpm | ~250 nm-1 µm | Nano/microspheres (FIG. 2h) |

Example 4

Determining the Protein Loading Efficiency of Poly-(AAm-co-AAPBA-co-DMAEMA)-PVA Microspheres and Poly-(NIPAAm-co-AAPBA-co-DMAEMA)-PVA Nano/Microspheres Protein loading efficiency of the compositions of the present technology were performed in triplicate. Ten milligrams of micro-/nanospheres were accurately weighed and 100 mM fructose-phosphate buffer saline (PBS) solution (2 mL, pH~6) was added to them. The solutions were sonicated for 30 min. at 37° C. and then vortexed for 48 h at room temperature. The solutions were centrifuged at 21382×g (HermLe Z 323, Germany) for 30 min. The supernatant was collected and its protein content was measured using Bradford reagent. The supernatant (20 µl) was added to Bradford reagent (1 mL) and mixed gently but thoroughly. After 10 min, the colour developed was read at 595 nm with help of a spectrophotometer. Based on standard plots for BSA, the actual protein loading was determined. Encapsulation efficiency (%) was determined using the formula:

Encapsulation Efficiency (%)=100×Actual Protein Loading/(Theoretical Protein Loading)

The use of the term encapsulation efficiency is not intended to imply that the protein or biological material is encapsulated, but rather that protein or biological material is entrapped within the polymer matrix or is bound to the surface of the particles of polymer.

Example 5

Analyte Responsive Particulates: In Vitro BSA Release from Microspheres and Nano/microspheres in Response to Monosaccharides To test the monosaccharide induced protein release from BSA containing poly-(AAm-co-AAPBA-co-DMAEMA)-PVA microspheres and poly-(NIPAAm-co-AAPBA-co-DMAEMA)-PVA nano/microspheres, and glucose (20 mM and 100 mM) were employed. Phosphate buffer (10 mM, pH~7.4), without any sugar, was used as control. Fifteen milligrams of particulates were accurately weighed into 2.0 mL microcentrifuge tubes and glucose-phosphate buffer solution (1.5 mL, pH~7.4) of specific glucose concentration was added into each tube. The tubes were incubated under gentle shaking (180 rpm) at 37° C. At each interval (regular intervals of 2 hours for the first 16 hours, then at 12 hour intervals to 52 hours, and finally at one day intervals up to 108 hours), the tubes were centrifuged at 6082×g (HermLe Z 323, Germany) for 10 min and supernatants (1 mL from each tube) were collected. The pellets were re-suspended in 1 mL of fresh glucose-phosphate buffer solutions. The released protein in the supernatant was quantified using Bradford reagent for protein estimation. The supernatant (20 µl) was added to Bradford reagent (1 mL), and mixed thoroughly. After 10 min, the absorbance of the mixture was measured at 595 nm using a spectrophotometer. Each release testing involving a specific glucose concentration or control was carried out in a triplicate. At the end of release studies, the percentage cumulative release of BSA from the particulates was plotted against the time in hours.

Poly-(AAm-co-AAPBA-co-DMAEMA)-PVA microspheres showed a protein loading efficiency of 81.46±3.66% and poly-(NIPAAm-co-AAPBA-co-DMAEMA)-PVA nano/microspheres showed a protein loading efficiency of 83.2±4.5%. Without being bound by mechanism, the protein encapsulation efficiencies observed for the PCC-PVA microspheres and nanospheres were due to the water-in-oil emulsion system designed for the particulate synthesis. Since the continuous oil phase of the emulsion (liquid paraffin light) forms an insoluble medium for the water soluble protein (BSA), efficient protein loading was observed.

Example 5A

Figure 3:
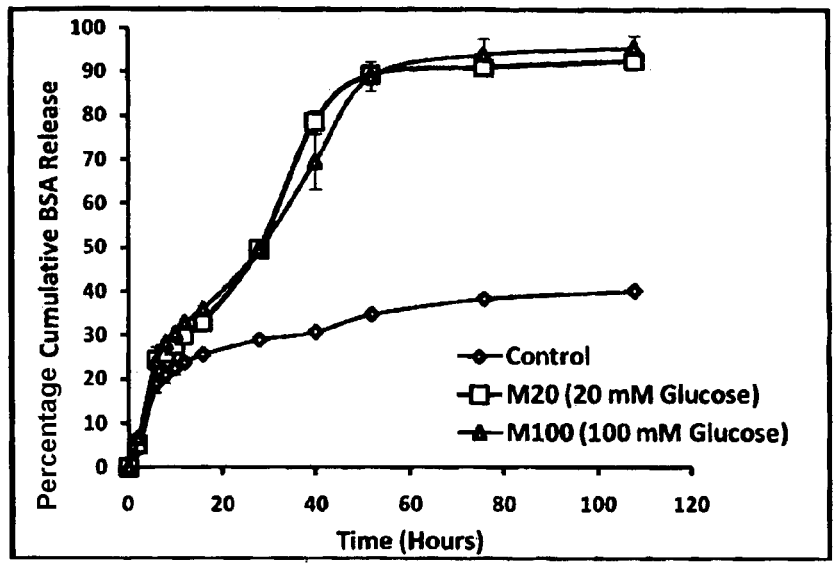
FIGS. 3A and 3B are protein release profile graphs for protein release from protein-containing PCC-PVA compositions, according to various embodiments.
Figure 3:
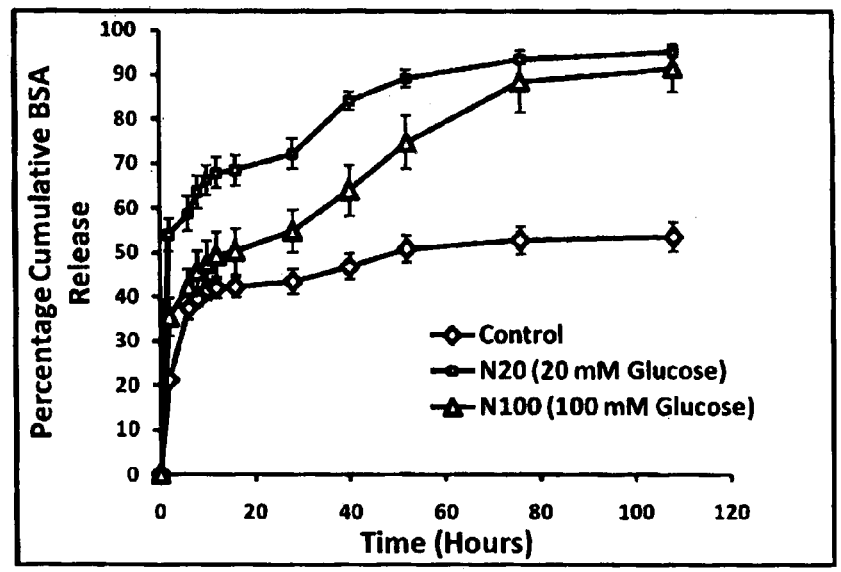

In Vitro BSA Release Studies from Poly-(AAm-co-AAPBA-co-DMAEMA)-PVA Microspheres The BSA release profiles of poly-(AAm-co-AAPBA-co-DMAEMA)-PVA microspheres in phosphate buffer (control), in 20 mM glucose-buffer solution (M20) and in 100 mM glucose-buffer solution (M100) are shown in FIG. 3a. The amounts of BSA released from M20 and M100 microspheres are much higher than those released from the control. After 108 h, M20 and M100 showed 92.413% and 95.5% protein release whereas control recorded only 40% release.

The protein release profiles of the controls show 2 prominent phases, an initial burst release phase (0-12 h) accounting for 25% of protein release, followed by a secondary slower phase (12-52 h), which gradually plateaus. The initial burst release can be attributed to the release of the surface bound protein that can be easily removed from the surface. A small amount of protein released by diffusion through microsphere matrix contributed to the secondary slower release phase.

The stationary or plateau phase characterized by very low protein release indicates the intact nature of microspheres in the absence of sugar. On the other hand M20 and M100 microspheres exhibited almost similar profiles of protein release with an initial burst release phase (0-12 h) followed by a slightly slower but still linear secondary release phase (12 h-52 h) which reaches a plateau after 52 h. The initial burst release associated with M20 and M100 microspheres showed relatively higher rates of protein release than the burst release phase of the control.

Based on these results, it is possible that, along with the easily removable surface bound protein, the matrix entrapped protein that was released in response to glucose induced matrix erosion also contributed to the burst release. After most of the surface bound protein was released, the matrix entrapped protein was released, which contributed to the secondary linear phase of protein release. By 52 h, almost 90% of the protein was released and the release profile began to reach a plateau. For M20 and M100 microspheres, during the protein release testing, the amount of the visible pellet collected at the bottom of the tube in each centrifugation step was observed to decrease with time also confirming the glucose induced microsphere erosion.

Example 5B

In Vitro BSA Release Studies from Poly-(NIPAAm-co-AAPBA-co-DMAEMA)-PVA Nano/Microspheres The BSA release profiles of BSA containing poly-(NIPAAm-co-AAPBA-co-DMAEMA)-PVA nano/microspheres in phosphate buffer (control), in 20 mM glucose-buffer solution (N20), and nano/in 100 mM glucose-buffer solution (N100) are shown in FIG. 3b. The amounts of BSA released from N20 and N100 nano/microspheres were considerably higher than those released from the control. After 108 h, N20 and N100 showed 95.0767% and 91.426% protein release whereas control recorded 53.565% release.

Similar to BSA containing poly-(AAm-co-AAPBA-co-DMAEMA)-PVA microsphere release profiles, the control recorded an initial burst release (0-12 hrs) accounting for 41.967% release of the protein followed by a secondary slower release phase (12-52 hrs) which gradually entered a plateau phase with negligible protein release.

Both the surface bound protein, and the matrix entrapped protein which is released in response to glucose induced particulate degradation, contributed to the markedly higher protein release associated with N20 and N100 nano/microspheres in comparison to the control in the burst release phase.

The glucose-induced release of the protein continued for up to 52 h (89.123% protein release) in N20 and up to 76 h (88.41% protein release) in N100 microspheres. After this secondary release phase the release profile gradually reached a plateau.

The amount of protein released in the form of burst release is considerably higher with nano/microspheres (41.9%) than with microspheres (25%). This may be due to the higher surface area of nano/microspheres which results in higher amounts of easily removable surface bound protein. As a result, the amounts of matrix entrapped protein may be lower for nanospheres than that for microspheres, which is indicated by the relatively slower release rates in the secondary release phase of N20 and N100 nano/microspheres when compared to M20 and M100 microspheres. Microspheres exhibited more stable protein release profiles in response to glucose, than did the nanospheres.

It may be noted that 100 mM glucose-buffer solution is not necessarily associated with faster protein release rates, when compared to 20 mM glucose-buffer solution. While the release profiles for both the glucose concentrations followed a similar pattern for the protein containing microspheres, for the of protein containing nano/microspheres, 20 mM glucose recorded slightly higher release rates in comparison to 100 mM glucose. Though 100 mM glucose efficiently erodes the PCC-PVA particulates, some amount of the entrapped protein may find it difficult to dissolve the bulk solution because of its high solute concentration (100 mM glucose in comparison with 20 mM glucose). As a result, some portion of BSA may still remain entrapped in the polymer matrix or surface bound on the particulate and stay with the pellet rather than dissolve in the supernatant during centrifugation. This may account for the lower release rates associated with 100 mM glucose-buffer solution.

These results demonstrate that these particulates may be useful as monosaccharide sensitive protein delivery systems to deliver proteins.

EQUIVALENTS

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms 'comprising,' 'including,' 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compounds, compositions, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, or compounds, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Finally, as will be understood by one skilled in the art, a range includes each individual member.

Other embodiments are set forth in the following claims.

What is claimed is:

1. A particulate comprising a composition comprising polyvinyl alcohol and a co-polymer;
wherein the co-polymer is:
poly-((acrylamide)$_m$-co-(N-acryloyl-3-aminophenylboronic acid)$_n$-co-(N,N-dimethylaminoethylmethacrylate)$_p$);
poly-((N-isopropylacrylamide)$_m$-co-(N-acryloyl-3-aminophenylboronic acid)$_n$-co-(N,N-dimethylaminoethylmethacrylate)$_p$);
poly-((N-isopropylacrylamide)$_m$-co-(4-vinylphenylboronic acid)$_n$-co-(N,N-dimethylaminoethylmethacrylate)$_p$);
poly-((acrylamide)$_m$-co-(4-vinylphenylboronic acid)$_n$-co-(N,N-dimethylaminoethylmethacrylate)$_p$); or
poly-((N,N-dimethylacrylamide)$_m$-co-(4-vinylphenylboronic acid)$_n$-co-(N,N-dimethylaminoethylmethacrylate)$_p$);

wherein,
m is from 150000 to 220000;
n is from 4000 to 6000; and
p is from 3500 to 5500.

2. The particulate of claim 1, wherein the particulate is a sphere.

3. The particulate of claim 2, wherein the sphere has a diameter from 200 nm to 50 μm.

4. A method of preparing a particulate, the method comprising:
adding separately to an oil phase, a polyvinyl alcohol, a radical initiator, a compound of Formula II, a compound of Formula III, and a compound of Formula IV to form a mixture; and
polymerizing the mixture to form a particulate of:
poly-((acrylamide)$_m$-co-(N-acryloyl-3-aminophenylboronic acid)$_n$-co-(N,N-dimethylaminoethylmethacrylate)$_p$);
poly-((N-isopropylacrylamide)$_m$-co-(N-acryloyl-3-aminophenylboronic acid)$_n$-co-(N,N-dimethylaminoethylmethacrylate)$_p$);
poly-((N-isopropylacrylamide)$_m$-co-(4-vinylphenylboronic acid)$_n$-co-(N,N-dimethylaminoethylmethacrylate)$_p$);
poly-((acrylamide)$_m$-co-(4-vinylphenylboronic acid)$_n$-co-(N,N-dimethylaminoethylmethacrylate)$_p$; or
poly-((N,N-dimethylacrylamide)$_m$-co-(4-vinylphenylboronic acid)$_n$-co-(N,N-dimethylaminoethylmethacrylate)$_p$);
where m is from 150000 to 220000; n is from 4000 to 6000; and p is from 3500 to 5500;
wherein:

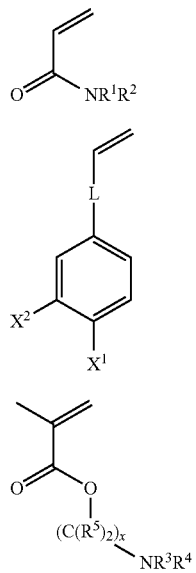

Formula II

Formula III

Formula IV wherein
L is a bond or —CONH— wherein the nitrogen is attached to the substituted phenyl group;

$R^1$ and $R^2$ are each H or each methyl, or $R^1$ is H and $R^2$ is iso-propyl;
$R^3$ and $R^4$ are each methyl;
$R^5$ is H;
x is 2; and
either $X^1$ is H and $X^2$ is —B(OH)$_2$, or $X^1$ is —B(OH)$_2$ and $X^2$ is H.

5. A method of releasing a protein from a particulate, the method comprising contacting the particulate with a monosaccharide to release the protein;
wherein the particulate comprises a composition comprising a protein, polyvinyl alcohol, and a co-polymer;
the co-polymer is:
poly-((acrylamide)$_m$-co-(N-acryloyl-3-aminophenylboronic acid)$_n$-co-(N,N-dimethylaminoethylmethacrylate)$_p$);
poly-((N-isopropylacrylamide)$_m$-co-(N-acryloyl-3-aminophenylboronic acid)$_n$-co-(N,N-dimethylaminoethylmethacrylate)$_p$);
poly-((N-isopropylacrylamide)$_m$-co-(4-vinylphenylboronic acid)$_n$-co-(N,N-dimethylaminoethylmethacrylate)$_p$);
poly-((acrylamide)$_m$-co-(4-vinylphenylboronic acid)$_n$-co-(N,N-dimethylaminoethylmethacrylate)$_p$; or
poly-((N,N-dimethylacrylamide)$_m$-co-(4-vinylphenylboronic acid)$_n$-co-(N,N-dimethylaminoethylmethacrylate)$_p$);
wherein,
m is from 150000 to 220000;
n is from 4000 to 6000;
p is from 3500 to 5500; and
the protein comprises a hormone, a growth factor, a cytokine, a soluble receptor, an enzyme, a monoclonal antibody, a peptide vaccine, or bovine serum albumin.

6. The particulate of claim 1 further comprising a protein, wherein the protein comprises a hormone, a growth factor, a cytokine, a soluble receptor, an enzyme, a monoclonal antibody, a peptide vaccine, or bovine serum albumin.

7. The particulate of claim 6, wherein the protein comprises insulin, vasopressin, calcitonin, growth hormone, luteinizing hormone releasing hormone, erythropoietin, insulin-like growth factor, epidermal growth factor, nerve growth factor, IL-1α, interferon α, interferon γ, interleukin 2, tumor necrosis factor receptor, asparaginase, prolidase, lysozyme, streptokinase, urokinase, group B *streptococcus* antigen vaccine, tetanus toxoid, diphtheria toxoid, encephalitis virus vaccine, or bovine serum albumin (BSA).

8. The particulate of claim 7, wherein the protein is bovine serum albumin (BSA).

9. The method of claim 5, wherein the protein comprises insulin, vasopressin, calcitonin, growth hormone, luteinizing hormone releasing hormone, erythropoietin, insulin-like growth factor, epidermal growth factor, nerve growth factor, IL-1α, interferon α, interferon γ, interleukin 2, tumor necrosis factor receptor, asparaginase, prolidase, lysozyme, streptokinase, urokinase, group B *streptococcus* antigen vaccine, tetanus toxoid, diphtheria toxoid, encephalitis virus vaccine, or bovine serum albumin (BSA).

10. The method of claim 9 wherein the protein is bovine serum albumin (BSA).

* * * * *